United States Patent [19]

Inoue et al.

[11] Patent Number: 5,360,722
[45] Date of Patent: Nov. 1, 1994

[54] METHOD AND APPARATUS FOR DETERMINING AIR BORNE BACTERIA

[75] Inventors: Keido Inoue, Takatsuki; Masaru Kawahashi, Toyonaka; Hisao Kinoshita, Nara; Kenji Mochida, Ibaragi, all of Japan

[73] Assignee: Kuraray Co., Ltd., Kurashiki, Japan

[21] Appl. No.: 7,004

[22] Filed: Jan. 21, 1993

Related U.S. Application Data

[63] Continuation of Ser. No. 674,973, Mar. 26, 1991, abandoned.

[30] Foreign Application Priority Data

Mar. 27, 1990 [JP] Japan .................................. 2-32431
Aug. 3, 1990 [JP] Japan .................................. 2-207254

[51] Int. Cl.$^5$ ............................ C12Q 1/04; C12M 1/34
[52] U.S. Cl. .............................. 435/34; 435/30; 435/291; 435/294; 435/311
[58] Field of Search ................ 435/30, 34, 290–293, 435/311, 313

[56] References Cited

U.S. PATENT DOCUMENTS

| | | |
|---|---|---|
| 3,001,914 | 9/1961 | Andersen .................. 435/30 |
| 3,127,329 | 3/1964 | Andersen ................ 435/30 X |
| 3,690,837 | 9/1972 | Witz et al. .............. 435/30 X |
| 3,713,987 | 1/1973 | Low et al. ............... 435/30 X |
| 3,741,877 | 6/1973 | Shaufus et al. ........... 435/30 X |
| 3,956,070 | 5/1976 | Kenyon . | 
| 4,182,656 | 1/1980 | Ahnell et al. ............... 435/34 |
| 4,336,337 | 6/1982 | Wallis et al. . |
| 4,971,900 | 11/1990 | Ahnell et al. ............... 435/29 |

FOREIGN PATENT DOCUMENTS 0122581  10/1984  European Pat. Off. .

OTHER PUBLICATIONS

Jost et al. *Applied Microbiology.* vol. 20. No. 6. 1970 pp. 861–865.

*Primary Examiner*—Robert J. Warden
*Assistant Examiner*—Krisanne M. Thornton
*Attorney, Agent, or Firm*—Oblon, Spivak, McClelland, Maier, & Neustadt

[57] ABSTRACT

A method for determining air borne bacteria which includes successive steps of passing a volume of air by a timed suction pump through a membrane filter at a membrane passing velocity of not more than 15 cm/sec and under a constant transmembrane pressure of not more than 100 mmHg to collect the air borne bacteria on the surface of the membrane filter. The membrane filter has a multiplicity of minute holes and is provided on a medium-absorbing pad housed in a holder. A medium is injected into the medium-absorbing pad housed in said holder. The bacteria thus collected are incubated and the number of the colonies developed on the surface of said membrane filter is measured.

7 Claims, 9 Drawing Sheets

METHOD AND APPARATUS FOR DETERMINING AIR BORNE BACTERIA

This application is a continuation of application Ser. No. 07/,674,973, filed on Mar. 26, 1991, now abandoned.

BACKGROUND OF THE INVENTION

1. Field of the Invention

The present invention relates to a method and apparatus for determining the density of microorganisms such as bacteria and fungi floating in the air (hereinafter referred to as "air borne bacteria").

2. Description of the Prior Art

Determination of the density (number per unit volume) of air borne bacteria is performed as one of the means to control the cleanliness in a room, to determine environmental pollution and like purposes. Falling bacteria method and collision method have been used for determining the density of air borne bacteria.

The former comprises allowing an open schale containing an agar medium to stand on a floor for a designate period to collect and incubate the bacteria falling from the air during the period and then measuring the number of colonies developed on the medium. This method, while having the advantage of ready measurement procedure, has problems of being incapable of conducting quantitative determination of the density of bacteria and of poor reproducibility caused by large variation in the values measured. The latter method comprises sucking a specified volume of air from the top of a measuring apparatus, and collide the sucked air onto an agar medium to collect bacteria, for which various measuring apparatuses are available. Slit-sampler type measuring apparatus is generally used for this purpose. This apparatus has on its top an air suction port comprising a narrow slit, through which air is blown onto a schale placed on a turn table mounted below the slit. The method, while being capable of conducting quantitative determination, has problems of the apparatus being expensive and the bacteria collected being readily affected by drying up because of high air flow rate.

In recent years, what is known as filtration method, utilizing a membrane filter, has been attracting much attention instead of the above falling bacteria and collision methods. This method comprises passing a specified volume of air intermittently through a membrane filter housed in a holder, thereby collecting bacteria on the surface of the membrane filter. The filter is then taken out from the holder and the bacteria collected on the filter surface is washed out into a liquid medium or the filter with the bacteria is laid on an agar medium to incubate the bacteria, followed by measurement of the number of the colonies developed on the surface of the membrane filter.

This filtration method has higher reproducibility and is better than falling bacteria method and collision method. The method however cannot be said to have high accuracy with sufficient reproducibility, since, when for example air borne bacteria in the same room are analyzed, the measurement data tend to vary to a large dispersion because of the bacteria dying out depending on the measuring conditions, e.g. rate and direction of air suction. Furthermore both the above collision and filtration methods require time-consuming sterilization and pasteurization of the apparatus used, preparation of medium and like preparations, and can be conducted only by skilled operators.

The large dispersion of measurement data in the filtration method is attributable firstly to the fact that, when air borne bacteria are collected through a membrane filter, the bacteria damage their cell membrane by collision against the membrane filter or die out due to intermittent application of pressures. It is therefore most important, for the purpose of increasing the reproducibility, to collect bacteria as they are, without killing them.

The large dispersion is secondly attributable to contamination of other bacteria occurring when the bacteria collected on the membrane filter is washed out on a liquid medium for incubation or the membrane filter with the bacteria is placed upon a medium, after the membrane filter with the bacteria has been removed from the holder.

SUMMARY OF THE INVENTION

Accordingly, an object of the present invention is to provide a method for determining with high reproducibility air borne bacteria which comprises collecting bacteria without extinguishing them and incubating them with no contamination of other bacteria.

Another object of the present invention is to provide a method for determining air borne bacteria which needs no previous complex operation of sterilization or pasteurization of the apparatus used or preparation of medium and can directly and readily be performed.

Still another object of the present invention is to provide an apparatus suited for conducting the above method.

The present inventors had studied how to surely collect air borne bacteria through a membrane filter without extinguishing them, by checking the survival ratio of bacteria when external force is applied thereto in the gaseous phase through observation of the change in the number of colonies incubated before and after the application. As a result it was found that bacteria do not die out when the external force applied thereto is below a specified level.

Thus the present invention is based on the finding that, when air borne bacteria are collected through a membrane filter, maintaining the differential of pressures applied on the front and back of the membrane filter (hereinafter referred to as "transmembrane pressure") below a specified level and with no pressure fluctuation and at the same time maintaining the air flow rate per effective area of the membrane filter (hereinafter referred to as "membrane passing velocity") below a specified level can surely prevent the bacteria from dying out, whereby measurement with high reproducibility is possible.

The above object can be achieved by a method for determining air borne bacteria which comprises successive steps of passing a volume of air by a suction pump means through a membrane filter at a membrane passing velocity of not more than 15 cm/sec and under a constant transmembrane pressure of not more than 100 mmHg to collect the air borne bacteria on the surface of said membrane filter, said membrane filter having a multiplicity of minute holes and provided on a medium-absorbing pad housed in a holder; injecting a medium into said medium-absorbing pad housed in said holder; incubating the bacteria thus collected; and measuring the number of the colonies developed on the surface of said membrane filter.

The present invention also provides an apparatus which comprises a holder equipped with an air inlet on the top and an air outlet on the bottom and housing a membrane filter having a multiplicity of minute holes and placed on a medium-absorbing pad, a pump means having an air suction port into which said air outlet of said holder can fit and sucking air via said membrane filter and a timer means that drives said pump means for a specified time.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
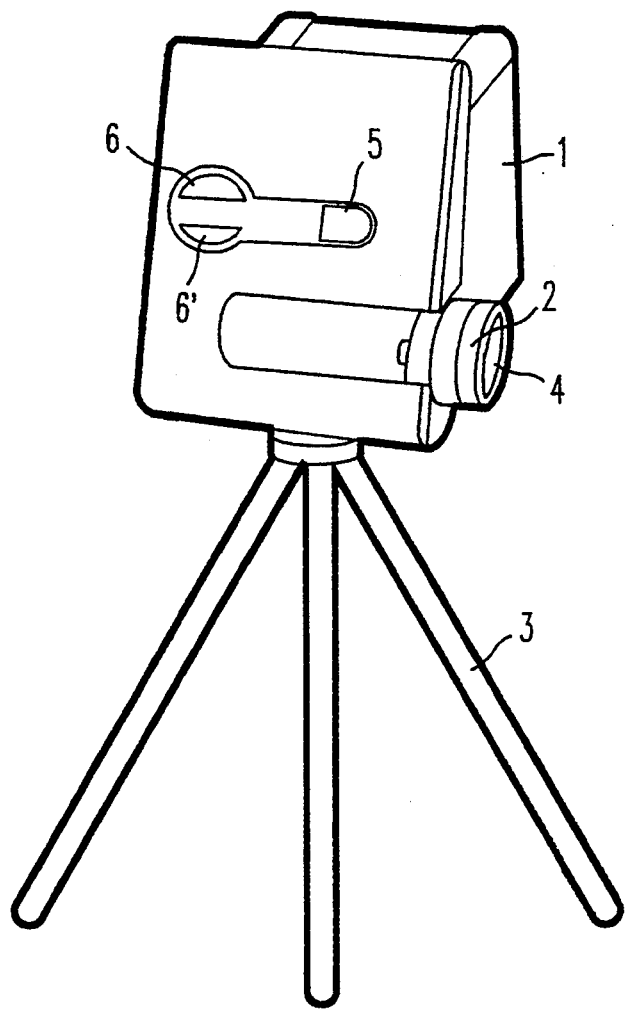
FIG. 1 is a drawing showing a perspective view of an example of the apparatus of the present invention fixed on a tripod.
Figure 2:
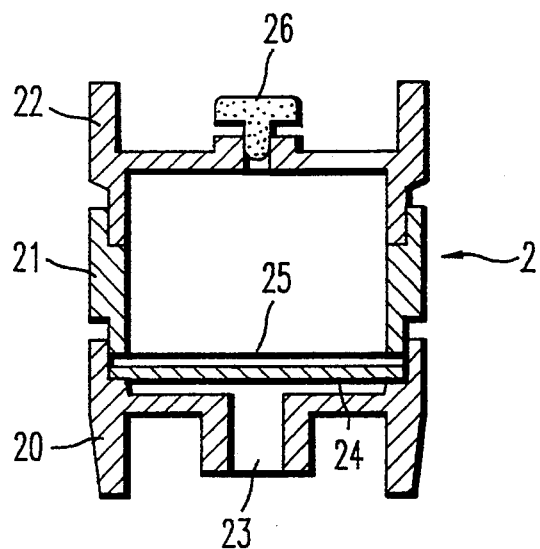
FIG. 2 is a cross-sectional view of an example of the holder used in the apparatus of the present invention.

FIG. 1 is a drawing showing a perspective view of an example of the apparatus of the present invention. This apparatus consists of a housing 1 housing a pump means (not shown) that sucks air and equipped on its side wall with an air suction port (not shown) and a holder 2 housing a membrane filter with a multiplicity of minute holes and equipped with an air outlet, the air outlet of the holder being inserted into the air suction port of the housing to mount the holder air-tight on the air suction port. The bottom of housing I is fixed on a tripod 3, which can change its height to set an air inlet 4 provided on the holder at a desired level. Air inlet 4 is generally set at a height 0.5 to 1.5 m from the floor level. 5 is a power source switch and 6 and 6' are each a switch for both setting running time of the pump means and starting it. Selection of start switch 6 runs the pump means for about 10 minutes and 6' for about 20 minutes.

FIG. 2 is a cross-sectional view of holder 2 to be fitted into the air suction port provided on the side wall of housing 1. The holder consists of a lower holder 20 having on its bottom an air outlet 23 and provided on its open top part with a medium-absorbing pad 24 and a membrane filter 25, a middle holder 21 with its bottom end contacting the periphery of membrane filter 25 to attach the membrane filter to the lower holder and its top end being open to constitute an air inlet, and an upper holder 22 optionally mountable or demountable on middle holder 21. The top end of upper holder 22 is provided with an opening and the opening is tightly stopped with a cap 26. The air space surrounded by middle holder 21 and upper holder 22 of holder 2 is sterilized by ethylene oxide gas. When the holder is used, upper holder 22 is demounted, and then air outlet 23 provided on the lower holder is fitted into the air suction port provided on housing 1. The fitting part has a structure being demountable and preventing bacteria in the room from invading the holder.

The holder 2 used in the present invention is made of a transparent plastic material, e.g. polycarbonate, polypropylene and styrene-acrylonitrile copolymer, so that the number of the colonies incubated in the holder can visually be counted from outside.

The membrane filter 25 housed in the holder is a film made of nitrocellulose, cellulose acetate, polyether sulfone, polycarbonate or the like and having a multiplicity of dense minute holes with nearly uniform diameter. Conventional filters are formed by entanglement of a multiplicity of filaments and hence have minute holes having irregular shapes, whereby the separatability of bacteria by filtration is insufficient. On the other hand, membrane filters have uniform-shape minute holes and are hence characterized by their very sharp separatability of bacteria. For the purpose of collecting air borne bacteria, membrane filters with a hole diameter of 0.2 to 0.8 $\mu$, preferably 0.2 to 0.45$\mu$ are generally used. It is preferred to use a membrane filter provided with a grating mark with a pitch of for example 2 to 3 mm, so that the number of colonies, after the bacteria collected have been incubated, can readily be counted. The membrane filter is laminated on its back surface with a medium-absorbing pad comprising a nonwoven fabric or the like made of a hydrophilic fiber such as cellulose, whereby the membrane filter can incubate air borne bacteria collected thereon by impregnating the pad with a medium.

It is necessary to use a pump means capable of maintaining always constant the flow rate of air sucked. Conventional vacuum pumps of rotary or piston type however cause a considerable fluctuation of flow rate when the resistance of the pass from an air suction port to discharge port changes and, further, generate instantaneous pulsation of flow rate as well as large noise. Furthermore, if a vacuum pump of rotary type or piston type, which is heavy and generally placed on the floor, is used, it must be connected to the holder for collecting air borne bacteria through a pipe or the like. Then, the air pass will become long and the connecting pipe will tend to change its shape, whereby the resistance to air flow changes and the flow rate fluctuates. Accordingly, it is important to select a pump having a structure that causes no change in air flow rate or pulsation, since bacteria are liable to be affected by external forces.

As a result of study on conventional pump means, it was found that diaphragm pumps are of low noise, cause almost no instantaneous pulsation of flow rate and can directly be connected to the holder because of their light weight, whereby it is possible to house entire apparatus in a housing. Thus, the air pass between an air suction port and discharge port can be made short and therefore the resistance to air flow is constant and the flow rate fluctuates only to a very small extent. Accordingly diaphragm pumps are very well suited for the pump means to be used in the present invention.

Diaphragm pumps however repeat suction and discharge intermittently and hence inevitably affect bacteria adversely. To overcome this, the use of at least 2 sets of diaphragm pumps can assure sucking air always at a constant flow rate and under a constant pressure. The pump structure was also studied for the purpose of obtaining a compact pump means, and it has been found that the pump means shown in FIG. 3 is most suited for the method and apparatus of the present invention.

Figure 3:
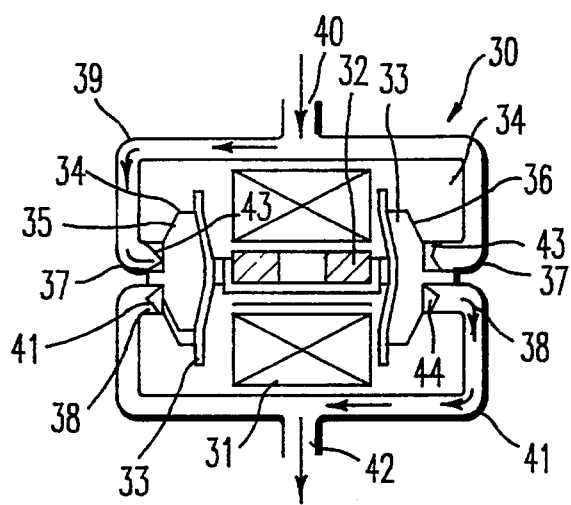
FIG. 3 is a drawing showing the operation principle of an example of the pump means used in the apparatus of the present invention.

FIG. 3 is a drawing showing the operation principle of an example of the pump means 30 used in the apparatus the present invention, where a first and second diaphragm 33 are mounted on both ends of a movable shaft 32 which strokes horizontally and reciprocally between a pair of electromagnets 31. The two diaphragms and a pump housing 34 form a first and second air chambers 35 and 36. The first and second air chambers are each provided with an air suction port 37 and air discharge port 38. The air suction ports 37 of first and second air chambers 35 and 36 are connected with each other by an suction pipe 39, which is equipped with a branch having on its end an air suction port 40 to mount a holder housing a membrane filter. The air discharge ports 38 are connected with each other through an air discharge pipe 41 equipped with a branch having on its end an air discharge port, 42 through which air is discharged.

The air suction ports 37 of first and second air chambers 35 and 36 are each equipped with a check valve 43 that closes during the compression movement and opens during the restoration of the diaphragms 33. On the other hand, the air discharge ports 38 are each equipped with a check valve 44 that opens during the compression and closes during the restoration of the diaphragms 33. Such being the structure, intermittent turning on of electromagnets 31 causes movable shaft 32 to stroke at a high speed so that the diaphragms alternately repeat compression and restoration, whereby air is continuously sucked through air suction port 40.

The pump means shown in FIG. 3 is compact and light because of its structure comprising two diaphragms mounted on both ends of a movable shaft, and can hence be mounted on a tripod. Furthermore the pump means, being directly connected to a holder, causes no flow rate fluctuation that would occur if a pump means be connected to a holder through a long pipe.

The pump means of the present invention need not be a structure as shown in FIG. 3 that consolidates a pair of diaphragm pumps into a compact body and comprises a movable shaft with its both end provided with a pair of diaphragms. For example at least 2 sets of independent diaphragm pumps connected with one another through a pipe can also be used. In this case it is necessary for the purpose of continuously sucking air, to mount check valves on the air suction ports and air discharge ports of the at least 2 diaphragm pumps in the same manner as shown in FIG. 3. The provision of these check valves assures a continuous suction of air even when at least 2 sets of diaphragm pumps are used.

Figure 4:
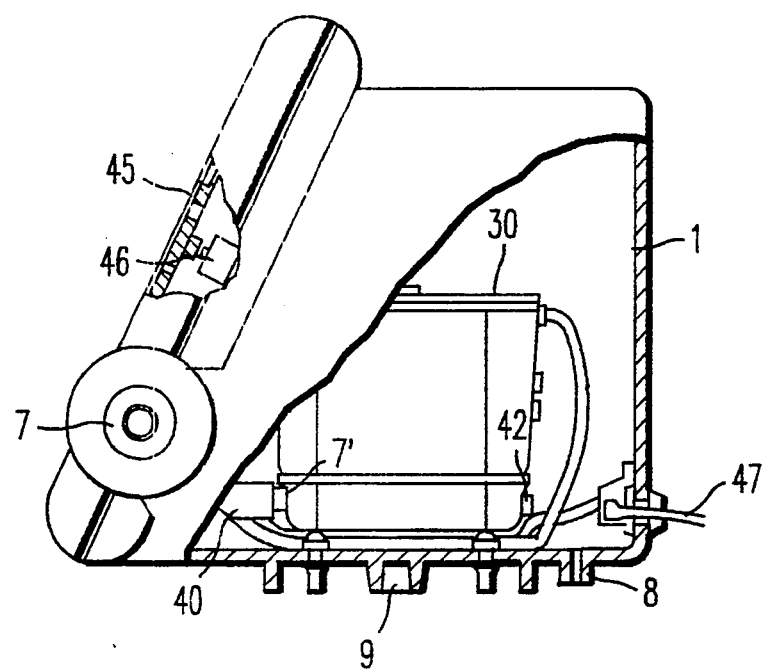
FIG. 4 is a cross-sectional view of an example of the apparatus of the present invention of which the pump means is housed in a housing.

FIG. 4 is a cross-sectional view of a housing 1 housing the above-described pump means 30, where an air suction port 7 provided on the side wall of the housing is connected through a pipe 40 to an air suction port 7' provided on pump means 30. The pipe 40 should be as short as possible to prevent air flow fluctuation. The bottom wall of the housing is provided with an air exhaust port 8 and a fitting 9 for tripods. The air exhaust port 8 discharges outwardly air delivered through the air discharge port 42. The air from the air discharge port can generally be delivered once into the housing and flown through a clearance between the pump means and the housing to cool the pump. Then, the pump means is protected from temperature elevation, and helps assure a stable air flow rate. This construction comprising a pump means 3 housed in a housing has another advantage of causing low noise.

The afore-described transmembrane pressure and membrane passing velocity of air can, with the membrane area of the membrane filter used being known, always be maintained at specified levels insofar as the pump means runs at a constant air suction rate and under a constant air pressure. For a pump means with large capacity, mounting a flow meter and a regulating valve can surely maintain the transmembrane pressure and the membrane passing velocity at below specified levels.

It is necessary that the apparatus of the present invention be equipped with a timer means, which permits air to flow at a constant rate for a constant period so that bacteria contained in a definite volume of air can be collected. It is preferred that the timer means used be capable of setting several different time levels, whereby the volume of air to be sampled can vary depending on the density of air borne bacteria to increase the accuracy measurement. The base panel 45 provided on the front of the housing shown in FIG. 4 is equipped with a switch for both starting the-pump means and setting its driving time. 46 is a control part housing the timer means. 47 is a power source cord. The apparatus of the present invention operates following the flow chart shown in FIG. 5.

Figures 5A, 5B:
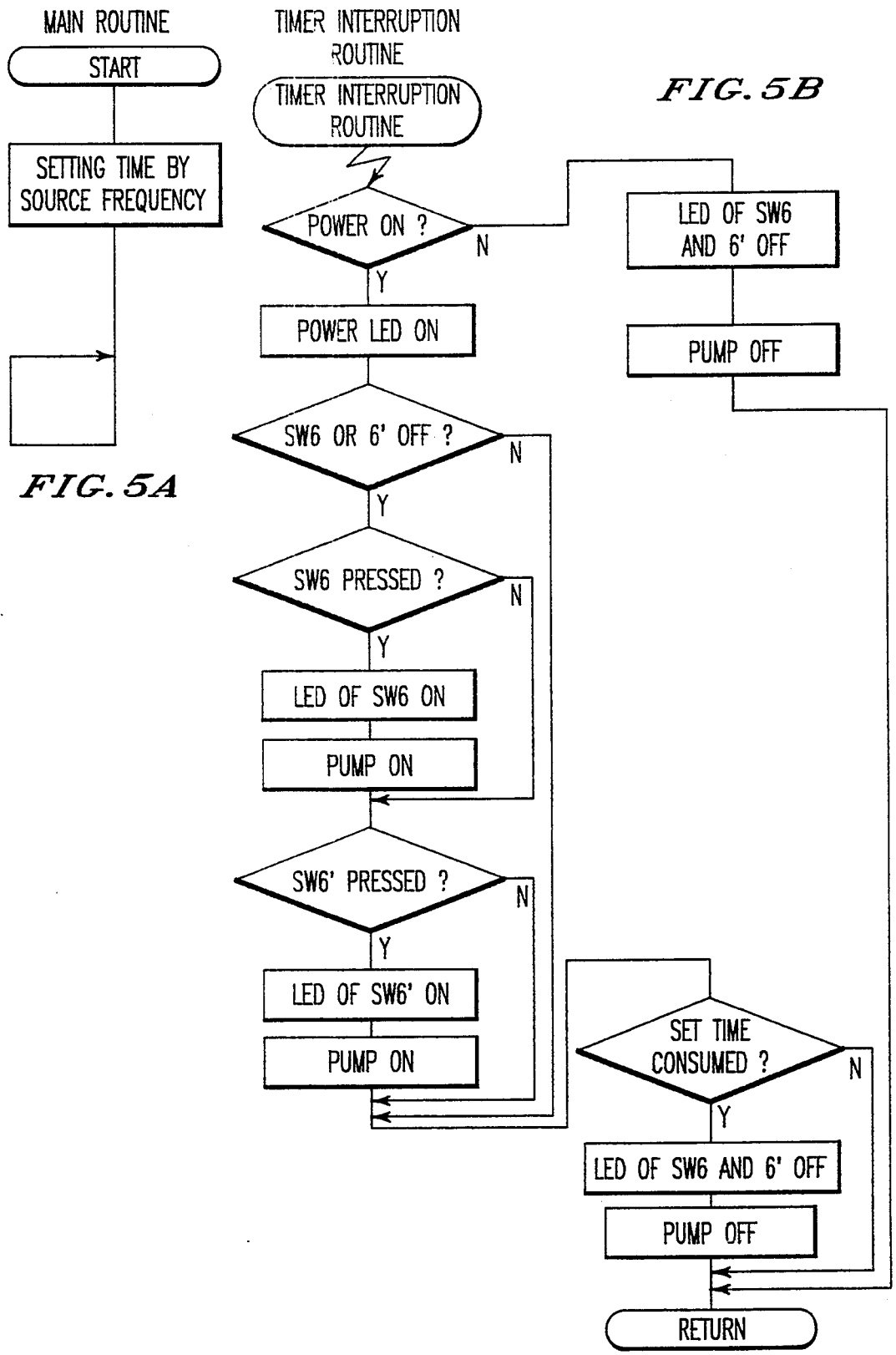
FIG. 5 is a flow chart showing the operation of the apparatus of the present invention.

In the apparatus of the present invention, timer interruption occurs for example every 1.95 ms to run timer interruption routine during running of main routine, as shown in FIG. 5. Switches 6 and 6' correspond to those shown in FIG. 1, switch 6 permitting the timer means to operate for about 10 minutes and switch 6' for about 20 minutes.

It has been found that, by sucking air under specified conditions and passing the air through a membrane filter under a constant transmembrane pressure using the apparatus of the present invention comprising the above-described construction, the bacteria in the sucked air can, without dying out, surely be collected on the surface of the membrane filter. It has also been found that the number of air borne bacteria can be determined in a very simple manner and in a closed system by using the specific holder housing the membrane filter and a medium-absorbing pad.

It has been clarified that there exists a close relationship between external forces applying onto bacteria and the dying out of the bacteria due to damage to their cell membrane. Further it has been clarified that there also is a close relationship between the membrane passing velocity at which air passes through the membrane filter and the survival ratio of the bacteria. Thus, where a transmembrane pressure of more than 100 mmHg or a membrane passing velocity of more than 15 cm/sec is employed, the survival ratio decreases with increasing transmembrane pressure or membrane passing velocity and the dispersion of measurement data markedly increases. The survival ratio has also been found to decrease when the pulsation of sucked air flow occurs. Consequently, one can cause almost no dying out of bacteria and minimize the dispersion of measurement data by maintaining the membrane passing velocity at which air passes through the membrane filter used at not more than 15 cm/sec and the transmembrane pressure constantly at not more than 100 mmHg.

In the sampling of air for determining air borne bacteria, air can be passed through the membrane filter in any direction, such as upward, horizontal or downward by placing the holder accordingly. The upward placing however sometimes causes the measurement data to vary because some other bacteria together with dust having adhered to the operator fall down onto membrane filter surface. To still increase the reproducibility of measurement data, the holder is therefore preferably placed horizontally so that the air flow passes through the membrane filter horizontally.

Now described is a process for determining air borne bacteria by the use of the apparatus of the present invention.

Figure 6:
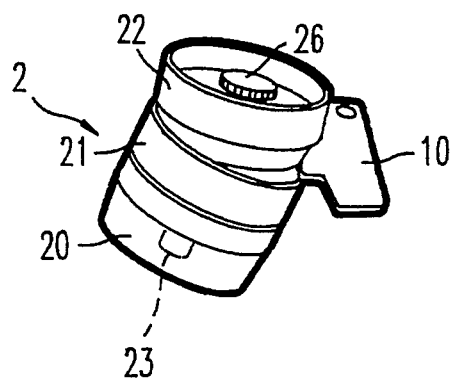
FIG. 6 is a perspective view showing an example of the apparatus of the present invention comprising a holder the upper part of which is removable.

Firstly, the power source switch of the apparatus shown in FIG. 1 is pressed, and then the upper holder 22 of holder 2 is removed as shown in FIG. 6 with a filter opener 10. Next, the air outlet 23 of the lower holder 20 is inserted into the air suction port 7 provided on the side wall of housing I and fixed there. Then the opening of the middle holder 21 becomes an air inlet.

After selection of desired suction time, starting switch 6 is pressed. The pump means starts running when the above switch is turned on and sucks air for about 10 minutes to collect bacteria onto the membrane filter surface. When the selected suction time is over, the switch turns off to stop the pump means.

Figure 7:
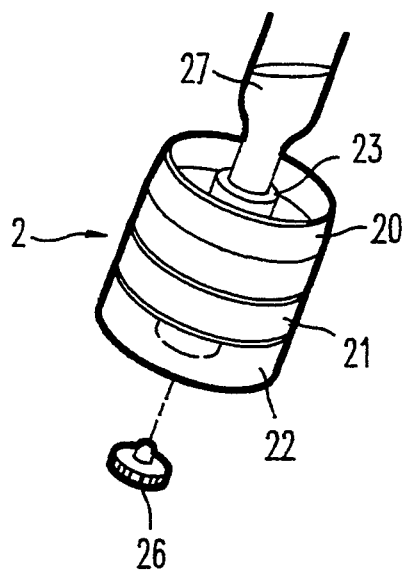
FIG. 7 is a perspective view showing how a medium is injected into the holder.

After the pump means has stopped, holder 2 is removed from the air suction port of the housing. The upper holder 22 is mounted on the middle holder of the demounted holder 2, to close the air inlet. Then the holder is turned upside down as shown in FIG. 7 and the end of an ampule 27 containing a medium is inserted into the holder through an air outlet 23 provided on lower holder 20 to inject a medium.

Since a medium absorbing pad is laminated on the back side of the membrane filter, a prescribed amount of the medium contained in the ampule readily impregnates the whole surface of the pad uniformly. Culture media are classified into those for bacteria in general and those for fungi, of which the former is used for incubating staphylococus or the like.

Examples of media for bacteria in general are a mixture of beef extract, tryptone, dextrose and the like and that of tryptone, soy peptone, sodium chloride, agar and the like.

Figure 8:
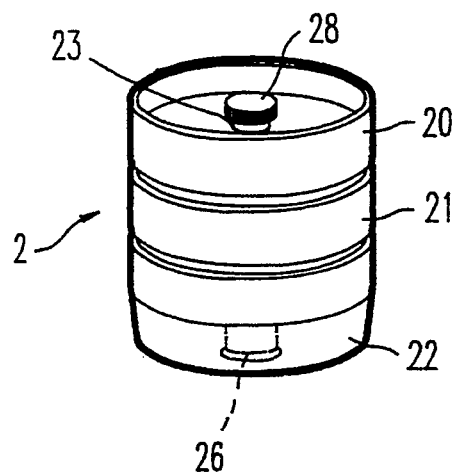
FIG. 8 is a perspective view of the holder into which a medium has been injected.

After completion of the injection of medium, the air outlet 23 provided on the lower holder is stopped tight with a cap 28 as shown in FIG. 8. It is preferred for the purpose of quickly impregnating the pad with the medium that a cap 26 stopping the air inlet of upper holder 22 be removed when the medium is injected- In this case the opening of upper holder 22 is stopped with cap 26 after injection of the medium has been complete.

Figure 9:
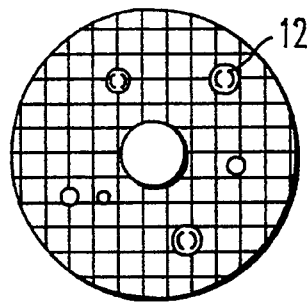
FIG. 9 is a plan view of a membrane filter on the surface of which bacterial colonies have developed.

A label indicating for example date and place of measurement, sample No. and the like is patched on the side wall of holder 2 stopped with cap 28, and the holder is, with the lower holder up, incubated in an incubator under prescribed conditions for a prescribed time. Bacteria in general are usually incubated for example at 35° to 37° for 24 to 48 hours. After the incubation time has elapsed, a number of colonies are observed on the surface of the membrane filter, as shown in FIG. 9. The number of the colonies is visually counted from over the transparent holder. The degree of pollution in the room tested can be judged based on the number of colonies per unit volume of air.

As described heretofore, the method and apparatus of the present invention can surely collect air borne bacteria without extinguishing them and thus provide high reproducible results. Besides, the method needs no preparation works and can be applied directly in a simple manner. The method is useful particularly for controlling cleanliness and checking the level of pollution in hospital rooms and the like where strict control on hygiene and environment is required.

Other features of the invention will become apparent in the course of the following descriptions of exemplary embodiments which are given for illustration of the invention and are not intended to be limiting thereof.

EXAMPLES

EXAMPLE 1

Figure 10:
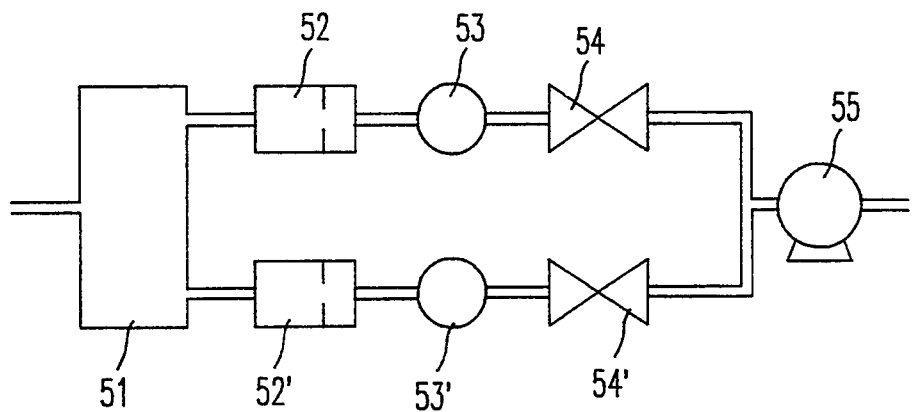
FIG. 10 is a schematic diagram of an experimental system for measuring the membrane passing velocity of air and the survival ratio of bacteria.
Figure 11:
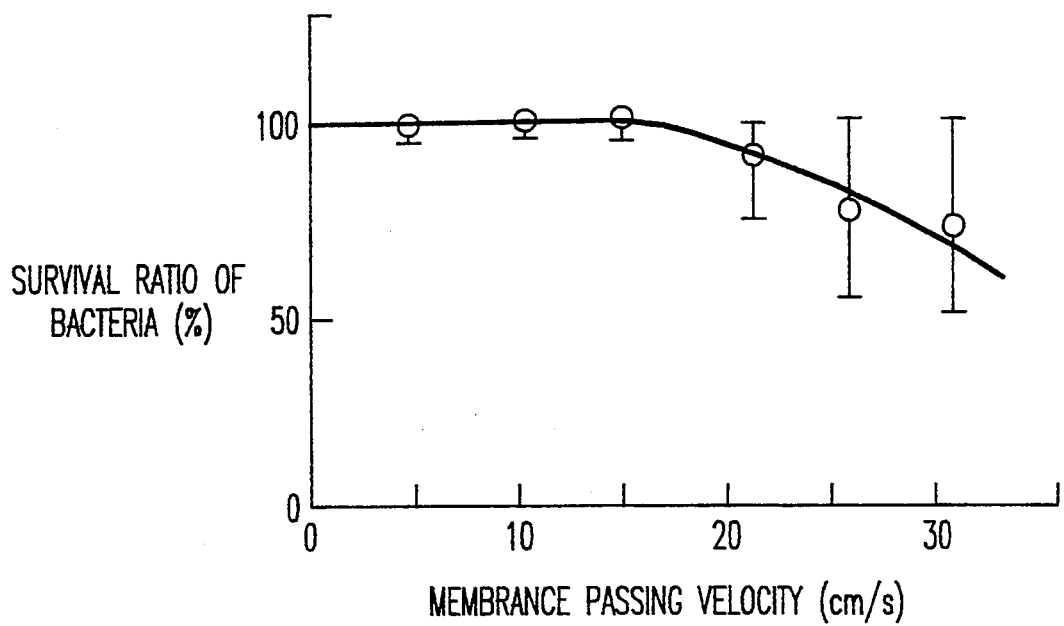
FIG. 11 is a graph showing the relationship between the membrane passing velocity of air and the survival ratio of bacteria.

The survival ratio of bacteria was studied by using an apparatus as shown in FIG. 10 and changing the membrane passing velocity of air passing a membrane filter. An air in a laboratory with a high degree of pollution was tested. The same air reservoir 51 was connected to a first holder 52 and a second holder 52' and the air was sucked by the same suction pump means 55 via flow meters 53 and 53' and regulating valves 54 and 54'. While the membrane passing velocity at the first holder 52 was kept constant, that at the second holder 52' was changed to measure the densities of escherichia and staphyrococcus, and the relationship between the membrane passing velocity and the survival ratio was studied. The results are shown in FIG. 11, where averages of 20 measurements were plotted with vertical bars indicating the range of measurement data.

As seen from the FIGURE, where the membrane passing velocity exceeds 15 cm/sec, the survival ratio decreases with increasing membrane passing velocity and the dispersion of measurement data markedly increases. It is therefore understood that maintaining the membrane passing velocity at 15 cm/sec or less can assures almost no dying out bacteria and minimize the dispersion of measurement data. Generally the membrane passing velocity is preferably 3 to 12 cm/sec to avoid adverse effects on bacteria.

EXAMPLE 2

Figure 12:
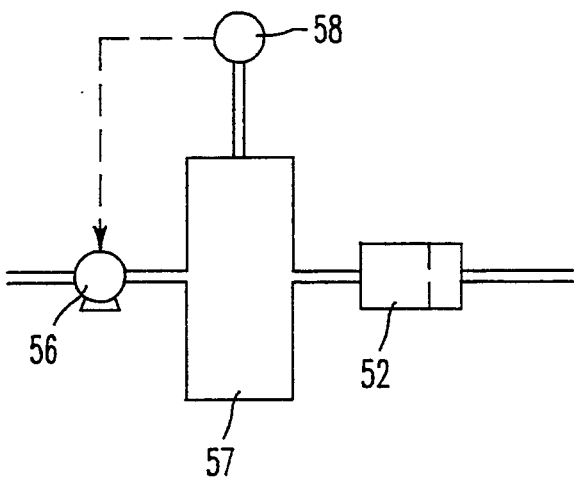
FIG. 12 is a schematic diagram of an experimental system for measuring the pressure applied on bacteria collected on a membrane and the survival ratio of the bacteria.

Air borne bacteria were collected onto the surface of a membrane filter of an apparatus as shown in FIG. 10. This procedure was repeated several times to prepare a plurality of first holders 52 having collected bacteria on the membrane filter surface. After the air outlets of the holders thus prepared had been opened, each of the holder was connected to an air suction pump means 56 via an air reservoir 57. The pump means was gang controlled, as shown in FIG. 12, with a pressure gauge 58 provided on the air reservoir 57 such that a constant pressure was applied on the membrane filter for 20 minutes. The indication by the pressure gauge corresponded to the transmembrane pressure the membrane filter.

The test was repeated with the pressure of the air reservoir, i.e. transmembrane pressure applied on the membrane filter, being changed. After each test the membrane filter was washed with a distilled water and the potassium ion concentration in the distilled water was determined.

When the cell membrane of bacteria is damaged, the potassium ions contained in their cell flow out into the distilled water. The change in the potassium ion concentration therefore indicates how their cell membrane is damaged, i.e. the degree of dying out of the bacteria.

Figure 13:
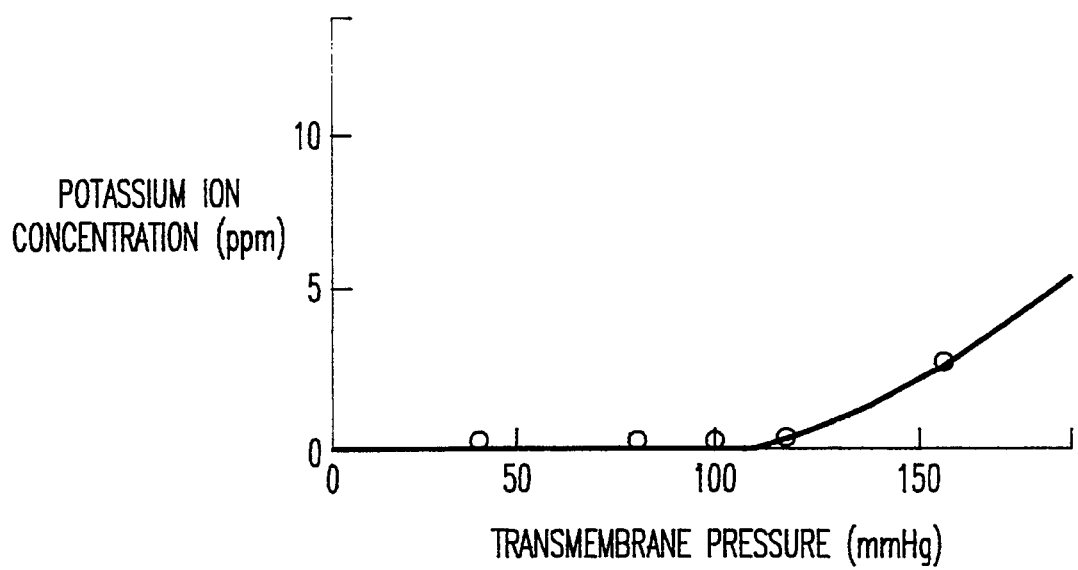
FIG. 13 is a graph showing the relationship between the transmembrane pressure and the survival ratio of bacteria.

FIG. 13 is a graph showing the relationship between the transmembrane pressure and the potassium ion concentration in the distilled water. As is seen from the FIG. 13, while with the transmembrane pressure being not more than 100 mmHg no appreciable flowing out of potassium ion into the aqueous solution occurred, with that exceeding 100 mmHg the potassium ion concentration increased with the transmembrane pressure, which clearly indicates the relationship between the transmembrane pressure and the survival ratio of bacteria. It is preferred in view of influence on bacteria that the transmembrane pressure be set at 10 to 75 cmHg.

EXAMPLE 3

Figure 14:
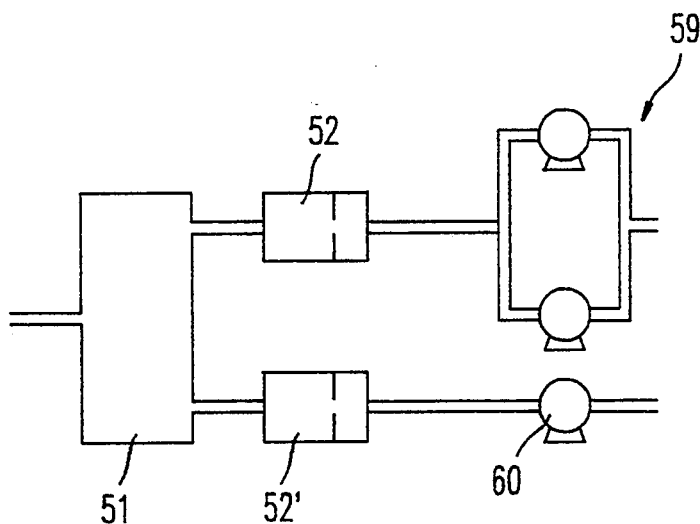
FIG. 14 is a schematic diagram of an experimental system for determining the influence of air flow pulsation on bacteria.

Influence of air flow pulsation on bacteria was studied using an apparatus as shown in FIG. 14. The specimen air was taken from a highly polluted laboratory as tested in Example 1. The same air reservoir 51 was connected to a first holder 52 and a second holder 52', and the first holder 52 was connected to a pump means 59 comprising 2 sets of diaphragm pumps to suck air continuously. The air suction ports and air discharge ports of the two diaphragm pumps were, as shown in FIG. 3, each equipped with a check valve, so that air was sucked under a constant pressure. A diaphragm pump 60 was mounted on the second holder 52'. With the membrane passing velocity being set at 12 cm/sec and the transmembrane pressure at not more than 100 mmHg, the pump means 59 connected to the first holder was run for 20 minutes and the diaphragm pump 60 connected to the second holder for 40 minutes.

Membrane filters housed in the above first and second holders were taken out and washed separately with an aqueous solution in the same manner as in Example 2. The aqueous solutions were tested for potassium ion concentration. While the potassium ion concentration of the membrane filter having been housed in the first holder was zero, that of the membrane filter in the second holder was 1.3 ppm. This fact indicates that bacteria will die out by intermittent application of pressure.

EXAMPLE 4

The apparatus of the present invention shown in FIG. 1 was placed at the center of a room to be tested for the density of air borne bacteria, with the holder being positioned such that air flowed horizontally at a height of 1 meter from the floor. A membrane filter having a diameter of 33 mm and provided with a grating mark of 3-mm pitch. A cellulosic-fiber nonwoven fabric was used as a medium-absorbing pad, which had an absorption capacity of about 1 ml. A capsule was mounted on the air suction port and the timer switched on. The pump ran for about 13 minutes. Air passes through the membrane filter horizontally at a membrane passing velocity of 8.8 cm/sec (4.5 l/min, 15° C.) to a total volume passed of 56.6 liters. The air sucked was discharged from an air discharge port provided on the housing.

After a designated volume of air had passed and the pump means had stopped, the upper holder was mounted on the air inlet of the holder to close the air inlet and the holder was demounted from the housing. About 1.0 ml of a medium was injected into the pad laminated on the back of the membrane filter. The medium had a composition of 6 g/l of beef extract, 10 g/l of tryptone and 2 g/l of dextrose.

The holder with the medium injected was placed in a incubator and incubated at 37° C. for 48 hours. Then, the number of colonies developed on the surface of the membrane filter was counted. The density of air borne bacteria was expressed in terms of pieces per cubic feet (pcs/cf).

Figure 15:
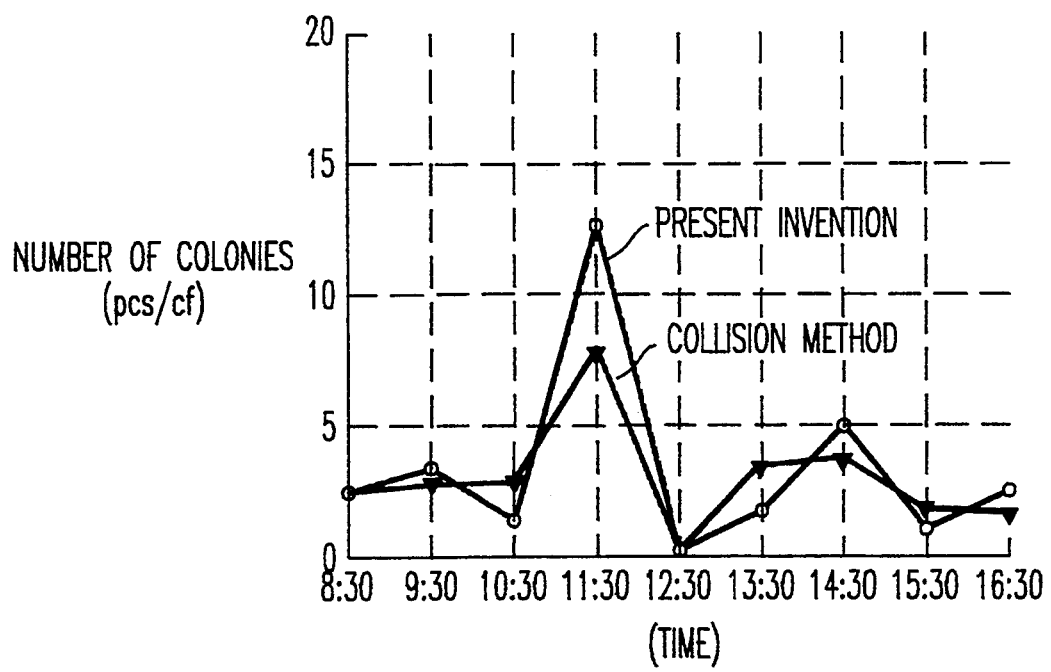
FIG. 15 is a graph showing the results of measurements of the number of air borne bacteria in a laboratory obtained with the apparatus of the present invention and those by a conventional collision method.

The air borne bacteria in the air off the laboratory was determined according to the above method. To confirm the accuracy of the measurement of the present invention, collision method, which is known to be a high-accuracy determination method, was also employed separately to determine air borne bacteria, which comprised sucking a designated volume of air from above a slit-type measuring apparatus and permitting the air to collide against an agar medium. The results obtained by the two methods showed, as shown in FIG. 15, a very high correlation.

Obviously, numerous modifications and variations of the present invention are possible in light of the above teachings. It is therefore to be understood that within the scope of the appended claims, the invention may be practiced otherwise than as specifically described herein.

What is claimed is:

1. A method for determining air borne bacteria which comprises successive steps of passing a volume of air by a suction pump means through a membrane filter at a membrane passing velocity of not more than 15 cm/sec and under a substantially constant transmembrane pressure of not more than 100 mmHg to collect the air borne bacteria on the surface of said membrane filter, said membrane filter being provided on a medium-absorbing pad housed in a holder; injecting a culture medium into said medium-absorbing pad housed in said holder; incubating the bacteria thus collected; and measuring the number of the colonies developed on the surface of said membrane filter.

2. A method according to claim 1, wherein said volume of air is passed horizontally through said membrane filter.

3. A method according to claim 1, wherein said volume of air is passed through said membrane filter while the transmembrane pressure is maintained substantially constant by combination of at least 2 sets of diaphragm pumps successively repeating compression and restoration.

4. An apparatus for determining air borne bacteria which comprises a holder equipped with an air inlet on the top and an air outlet on the bottom and housing a membrane filter, a pump means which has an air suction port constructed and arranged to receive said air outlet of said holder, which pump means sucks air via said membrane filter, and a timer that drives said pump means for a specified time, wherein said membrane filter is laminated on a medium-absorbing pad wherein said pump means comprises a pair of diaphragms provided on both ends of a reciprocally movable shaft constructed and arranged such that the strokes of said reciprocally movable shaft permit said pair of diaphragms to alternately repeat compression and restoration.

5. An apparatus according to claim 4, wherein said pump means is constructed and arranged to suck air via said membrane filter at a membrane passing velocity of not more than 15 cm/sec and under a constant transmembrane pressure of not more than 100 mmHg.

6. An apparatus according to claim 4, wherein said holder equipped with said membrane filter is installed at a vertical height from the floor of 0.5 to 1.5 m.

7. An apparatus according to claim 4, wherein said pump means comprises at least 2 diaphragm pumps, each of said diaphragm pumps having an air discharge port provided with a check valve constructed and arranged to open during compression and close during restoration and an air suction port provided with a check valve constructed and arranged to close during compression and open during restoration, said air suction ports of said diaphragm pumps being connected by a connecting pipe having an air suction port constructed and arranged to receive said air outlet of said holder, said diaphragm pumps sucking air continuously by successive repetition of compression and restoration of the diaphragms.

* * * * *